(12) United States Patent
Rueter et al.

(10) Patent No.: US 7,280,868 B2
(45) Date of Patent: Oct. 9, 2007

(54) CAPTURE MANAGEMENT IMPROVEMENTS

(75) Inventors: John C. Rueter, Woodbury, MN (US); Christopher M. Manrodt, White Bear Lake, MN (US); James W. Busacker, St. Anthony, MN (US); Todd J. Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 501 days.

(21) Appl. No.: 10/434,689

(22) Filed: May 9, 2003

(65) Prior Publication Data
US 2004/0030358 A1 Feb. 12, 2004

Related U.S. Application Data

(63) Continuation-in-part of application No. 10/004,164, filed on Oct. 30, 2001, now Pat. No. 7,027,868.

(51) Int. Cl.
*A61N 1/362* (2006.01)
(52) U.S. Cl. ........................................ 607/9
(58) Field of Classification Search .................. None
See application file for complete search history.

(56) References Cited

U.S. PATENT DOCUMENTS

| | | | |
|---|---|---|---|
| 4,476,868 A | 10/1984 | Thompson | |
| 5,052,388 A | 10/1991 | Sivula et al. | |
| 5,165,404 A | 11/1992 | Andersson et al. | |
| 5,165,405 A | 11/1992 | Eckwall | |
| 5,172,690 A | 12/1992 | Nappholz et al. | |
| 5,222,493 A | 6/1993 | Sholder | |
| 5,285,780 A | 2/1994 | Tsuji et al. | |
| 5,320,643 A | 6/1994 | Roline et al. | |
| 5,324,310 A | 6/1994 | Greeninger et al. | |
| 5,345,362 A | 9/1994 | Winkler | |
| 5,447,525 A | 9/1995 | Powell et al. | |
| 5,601,615 A | 2/1997 | Markowitz et al. | |
| 5,954,755 A * | 9/1999 | Casavant | 607/28 |
| 2002/0183798 A1 | 12/2002 | Vonk | 607/28 |
| 2003/0083712 A1 | 5/2003 | Rueter et al. | 607/28 |

FOREIGN PATENT DOCUMENTS

EP  1 116 495 A2  7/2001

* cited by examiner

*Primary Examiner*—Kristen Droesch Mullen
(74) *Attorney, Agent, or Firm*—Daniel G. Chapik

(57) ABSTRACT

A capture detection algorithm detects and distinguishes atrial capture. Atrial chamber reset (ACR) and AV conduction (AVC) algorithms are implemented to measure an atrial pacing threshold The data that is used to choose between ACR and AVC methods is used to determine the progression of the patient's disease state. Some of the significant aspects of the invention include enablement of accurate threshold measurements, including calculation of stability criteria, precise interval measurements and the use of reference interval to determine capture and loss of capture.

3 Claims, 13 Drawing Sheets

CAPTURE MANAGEMENT IMPROVEMENTS

RELATED APPLICATIONS

This application is a continuation-in-part of application number 10/004,164, filed Oct. 30, 2001, now U.S. Pat. No. 7,027,868 which is herein incorporated by reference in its entirety.

FIELD OF THE INVENTION

The present invention generally relates to implantable pacemakers and defibrillators and more particularly to a method and apparatus for testing and detecting capture of the heart in both chambers of the heart, deriving and storing stimulation signal threshold data, and adjusting stimulation signal energy for energy efficiency.

BACKGROUND OF THE INVENTION

As described in commonly assigned U.S. Pat. No. 5,320,643, incorporated herein by reference, a cardiac pacemaker is an electrical device implemented to rectify an abnormal heart's natural pacing function by delivering appropriately timed electrical stimulation signals designed to cause the myocardium of the heart to depolarize. Stimulation pulses provided by implanted pacemakers usually have well-defined amplitude and pulse width characteristics both of which can be adjusted by remote programming and telemetry equipment to meet physiologic and device power conservation needs of the particular therapy regimen of a patient.

The amplitude and pulse width of the pacing pulses must be of such a magnitude above the stimulation threshold to maintain capture so as to prevent serious complications. Yet, it is desirable that these pacing output parameters are no higher than a reasonable safety margin above the stimulation threshold in order to prolong battery life. The patient's stimulation thresholds in the atrium and ventricle often fluctuate in the short term, and gradually change over the long term. Clinical experience has shown that the lowest stimulation threshold is observed immediately after implantation of the pacemaker. Inflammation of the cardiac tissue around the tip of the pacing lead electrode can drive the stimulation threshold up sharply during the first two to six weeks after implant to its highest level, depending on the lead used. When the stimulation threshold rises, a greater pacing pulse magnitude is required to effect capture. Some of the inflammation reduces over the long-term, to lower the threshold below the peak level, to the chronic threshold level. However, the chronic threshold usually never is as low as the acute level, since some permanent fibrous tissue remains around the electrode tip. Thus, care must be taken to ensure output levels are programmed to magnitudes that maintain capture. On a daily basis, thresholds may decrease with exercise, for example, and may increase with various activities, including sleep. Consequently, the safety margin is typically set by the physician on implantation of the pacemaker to accommodate projected maximal stimulation thresholds and may be adjusted manually by the physician or automatically by the pacemaker to accommodate these changes during follow-up sessions.

As described in commonly assigned U.S. Pat. No. 5,324,310, incorporated herein by reference, the post-operative determination of the stimulation thresholds by the physician typically requires the patient to be connected to surface ECG equipment while a threshold routine is conducted using the pacemaker programmer. The pacemaker programmer successively reprograms the pulse width and/or amplitude on a temporary basis to ascertain the points at which capture is lost. The pacing pulses are observed on a display or paper tracing as spikes, and capture or loss of capture is observed by the presence or absence of the evoked cardiac response wave shape (a P-wave or an R-wave) that follows each spike. At loss of capture, the programmed pacing pulse may be immediately restored so that the patient does not experience syncope. A strength-duration curve may be plotted from the resulting threshold data. The resulting threshold data may then be used to permanently reprogram the pulse magnitude. Naturally, such periodic patient studies are time-consuming and expensive to conduct. Moreover, they do not provide an indication of stimulation threshold fluctuation over the course of a patient's day and levels of activity. If, however, the pacing pulse is of a greater magnitude than necessary to meet these changing levels of activity, the life of the implantable pulse generator (IPG) is shortened as the battery is depleted.

As a result of these considerations, a great deal of effort has been expended over many years to develop IPGs with the capability of automatically testing the stimulation threshold, i.e. providing an "auto-capture" detection function, and resetting the pacing pulse magnitude to exceed the threshold by a safety margin without the need for clinical or patient intervention. A wide variety of approaches have been taken, for example, in commonly assigned '310 and '643 patents and in U.S. Pat. Nos. 5,165,404, 5,165,405, 5,172,690, 5,222,493 and 5,285,780.

In such IPGs, the capture detection approaches have taken a variety of forms typically in an attempt to overcome the difficulty in detecting the evoked cardiac response waveform shape from the pacing electrodes employed to deliver the pacing pulse. A high energy pacing pulse and the ensuing after-potentials and electrode/tissue polarization artifacts may mask the evoked response, and may also saturate the sense amplifiers coupled to the electrodes, until they dissipate. By the time that the sense amplifier is no longer blinded, the evoked response, if any, has typically passed the electrodes. Many of these approaches include blanking intervals for the sense amplifiers. Such approaches are combined with other efforts to suppress, attenuate, or compensate electronically for the composite post-delivery signal levels at the sense amplifier to shorten the saturation period (and the blanking interval) as much as possible.

Alternatively, the use of separate "far-field" EGM amplifiers and electrode systems from those "near-field" electrode systems used in delivering the pacing pulse have been proposed in, for example, the above referenced '310 patent.

In a further approach, one or more physiologic sensors that show a response to the mechanical action of the heart, e.g. a piezoelectric or impedance sensor, or a response that shows changes in physical properties of the blood when the heart is captured, e.g. blood pH, temperature, impedance or blood pressure sensors on the pacing lead have also been suggested as disclosed by the above referenced '643 patent.

The function and accuracy of the these approaches are impacted by one or more of factors including, but not limited to: myopotentials (electrical signals which are the product of muscle movement) in the case of EGMs; stray electromagnetic interference (EMI); problems with the sensor sensitivity (either too sensitive or not sensitive enough); and, in the case of pressure sensors, variations of the sensed electrical signals as a result of changes in thoracic pressure (for example, due to respiration, coughing or sneezing).

Further, in U.S. Pat. No. 5,601,615 issued to Markowitz et al, which is incorporated herein in its entirety, another approach is disclosed. Atrial loss of capture (ALOC) in response to an A-pace test stimulus is determined by the absence of a detected ventricular depolarization (V-event) in the latter portion of the paced A-V delay interval following the delivery of the A-pace test stimulus. In another approach for use in the atrium in patients having regular measured sinus rhythm, premature A-pace test stimuli are delivered. The presence or absence of a sensed A-event at the end of the measured sinus escape interval determines whether capture or loss of capture at the test stimulus is present.

In regard to the prior art known to the inventors, with the exception of the '615 patent, it is necessary to rely on additional components and circuitry that consume more energy and add to the bulk and cost of the system in addition to reliability concerns. Further additional components and circuitry are increased in dual chamber pacemakers, for example, where the difficulty of detecting the evoked P-wave is further complicated by its relatively low amplitude. Hence, there is a need for an apparatus and method to distinguish between the presence or absence of sinus node disease (SND) and/or AV conduction block. There is a further need for yet another apparatus and method that would enable to indicate and evaluate the presence or absence of atrial capture.

SUMMARY OF THE INVENTION

The present invention provides a cardiac pacemaker with a capture detection algorithm in which atrial capture may be detected and distinguished without adding other components to the device. In addition, the present invention describes a method for an immediate measurement of the capture threshold whenever a pacemaker switches a lead's polarity from bipolar to unipolar in response to a detected lead failure in either one or both chambers.

Specifically, the present invention provides an Atrial Chamber Reset (ACR) method that functions in dual chamber pacemakers implanted in patients with some form of AV block and a healthy sinus node. ACR instructs the atrial output circuitry to emit atrial test pulses on a periodic basis at varying energies to determine the minimum magnitude of the test pulse that captures the atrial myocardium. ACR confirms atrial capture due to an atrial test pace by an interruption of a "stable" sinus rhythm previously observed in the patient.

The present invention also provides an AV Conduction (AVC) method that is specifically aimed at patients with an intact AV node. The normal pattern of pacing in such patients is atrial pace (AP) followed by ventricular sense (VS). AVC also uses atrial test pulses that, in this method, gradually drop from high to low energies or from low to high energies until loss of atrial capture (LOAC) occurs. "Backup" atrial paces will, however, immediately capture and restore AV synchrony after LOAC due to atrial test pulses. LOAC is marked by an interruption in the stable ventricular sensed rhythm that had been present following the previous atrial paced rhythm.

The present invention also provides means for determining the use of the AVC or ACR methods without user intervention. Prior to each test attempt, the algorithm determines which method is most likely to successfully measure an atrial pacing threshold in any given patient at any given time. By storing the data that led to the choice between methods, the present invention furnishes information to the user about the progression of the patient's disease state.

The present invention may be applied to a multi-programmable DDD(R) IPG, ICD, or other cardiac Implantable Medical Device (IMD) by simply storing the operating algorithm in hardware memory to periodically perform atrial threshold measurements. One of the novel aspects of the present invention is that it clearly defines what is required to ensure accurate threshold measurements, including calculation of the stability criteria, precise interval measurements, and the use of reference interval versus test intervals to determine capture and loss of capture. No additional circuitry, sensors or other components are necessary to practice these methods. The IPG is effectively reconfigured to apply atrial stimuli at varying pulse widths and amplitudes and to process these signals in order to declare atrial capture or LOAC. The part of the present invention that tests for a "failed" lead may be used in single or dual chamber devices and requires no further hardware. It simply stores for immediate use the operating algorithm Atrial Pacing Threshold Search (APTS) via the ACR or AVC methods for the atrium or Ventricular Pacing Threshold Search (VPTS) for the ventricle. This is implemented to effect threshold measurements whenever a suspected lead failure is detected and the device changes from the bipolar to unipolar operation on the implanted atrial or ventricular lead.

The present invention further includes software programs for executing methods and process described herein. The invention includes pacemakers with processors implementing the software programs/algorithms tailored to perform and execute the methods and process disclosed herein.

DETAILED DESCRIPTION OF THE DRAWINGS

Figure 1:
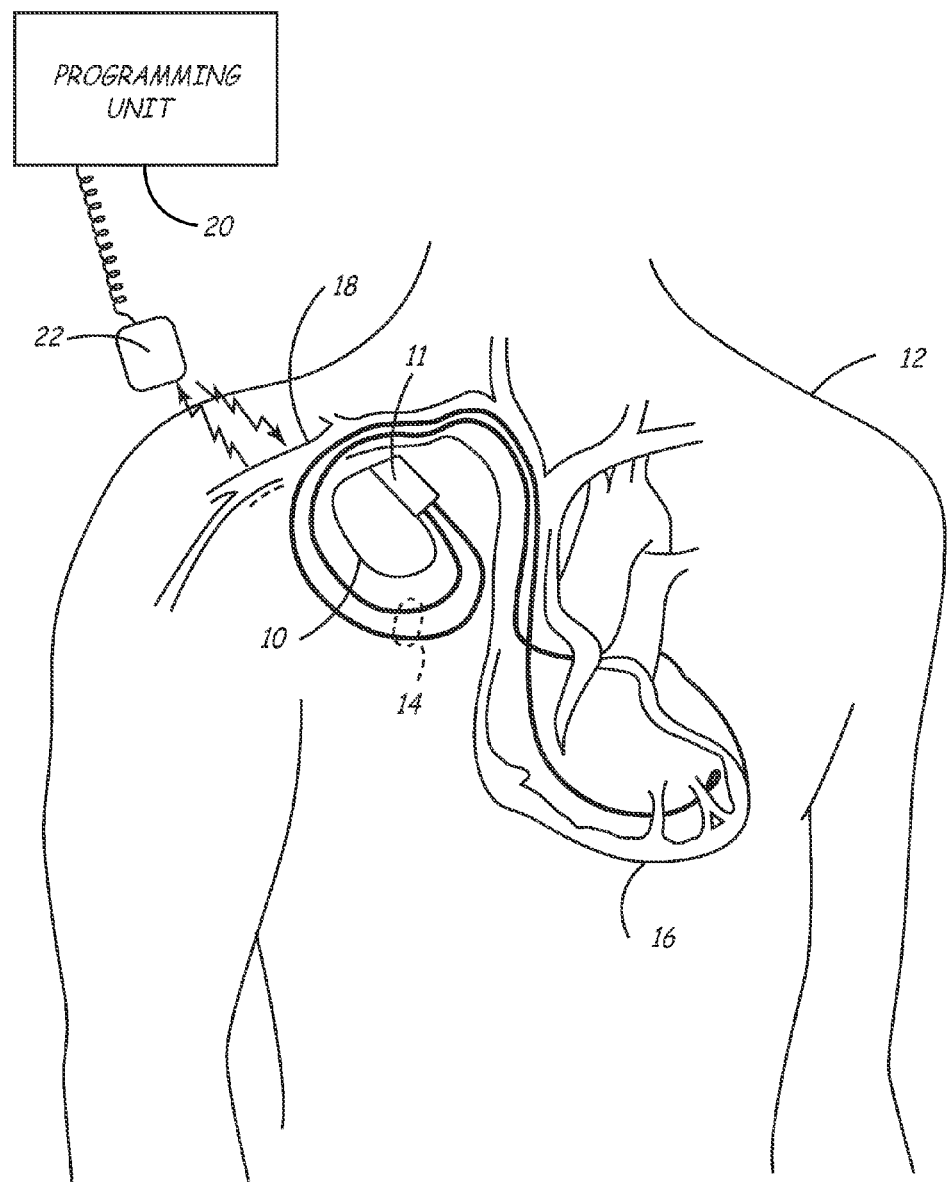
FIG. 1 is an illustration of a body-implantable device system in accordance with the present invention, including a hermetically sealed device implanted in a patient and an external programming unit.

FIG. 1 is an illustration of an implantable medical device system adapted for use in accordance with the present invention. The medical device system shown in FIG. 1 includes an implantable device 10 such as, for example, a pacemaker that has been implanted in a patient 12. In accordance with conventional practice in the art, pacemaker 10 is housed within a hermetically sealed, biologically inert outer casing, which may itself be conductive so as to serve as an indifferent electrode in the pacemaker's pacing/sensing circuit. One or more pacemaker leads, collectively identified with reference numeral 14 in FIG. 1 are electrically coupled to pacemaker 10 in a conventional manner and extend into the patient's heart 16 via a vein 18. The leads used may also be disposed on the external surface of the heart (not shown). Such leads are termed epicardial leads and are known to those skilled in the heart.

Disposed generally near the distal end of leads 14 are one or more exposed conductive electrodes for receiving electrical cardiac signals and/or for delivering electrical pacing stimuli to heart 16. As will be appreciated by those of ordinary skill in the art, leads 14 may be implanted with their distal end(s) situated in the atrium and/or ventricle of heart 16, in positions commonly known to those skilled in the state of the art such as, the apex of the right ventricle, atrial appendage, coronary sinus, among others.

Although the present invention will be described herein in an embodiment which includes a pacemaker, those of ordinary skill in the art having the benefit of the present disclosure will appreciate that the present invention may be advantageously practiced in connection with numerous other types of IMD systems, and indeed in any application in which it is desirable to provide a method to determine atrial thresholds in a dual chamber IMD.

Also depicted in FIG. 1 is an external programming unit 20 for non-invasive communication with implanted device 10 via uplink and downlink communication channels, to be hereinafter described in further detail. Associated with programming unit 20 is a programming head 22, in accordance with conventional medical device programming systems, for facilitating two-way communication between implanted device 10 and programmer 20. In many known implantable device systems, a programming head such as that depicted in FIG. 1 is positioned on the patient's body over the implant site of the device (usually within 2- to 3-inches of skin contact), such that one or more antennae within the head can send RF signals to, and receive RF signals from, an antenna disposed within the hermetic enclosure of the implanted device or disposed within the connector block of the device, in accordance with common practice in the art.

Figure 2:
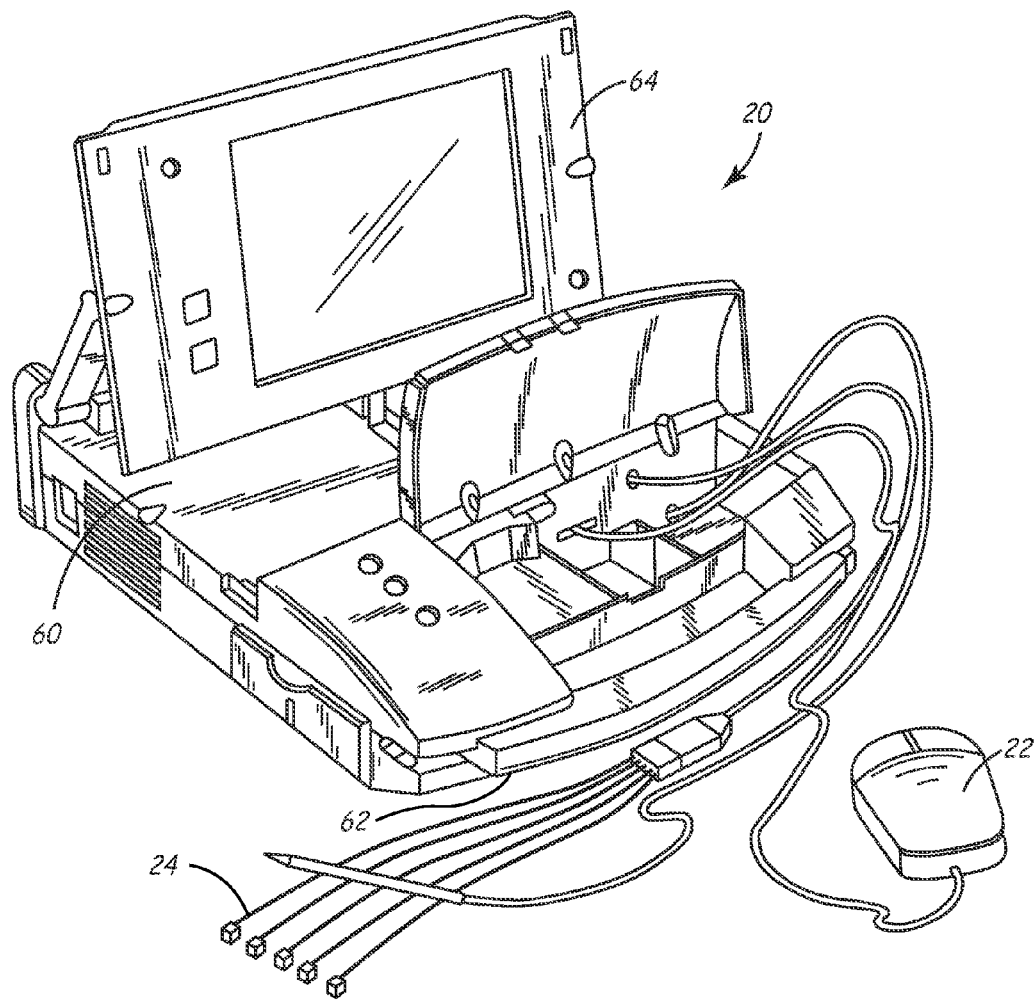
FIG. 2 is a perspective view of the external programming unit of FIG. 1.

FIG. 2 is a perspective view of programming unit 20 in accordance with the presently disclosed invention. Internally, programmer 20 includes a processing unit (not shown in this Figure) that in accordance with the presently disclosed invention is a personal computer type motherboard, e.g., a computer motherboard including an Intel Pentium 3 or later microprocessor and related circuitry such as digital memory. The details of design and operation of the programmer's computer system will not be set forth in all its elements in the present disclosure, as it is believed that such details are well-known to those of ordinary skill in the art.

Referring to FIG. 2, programmer 20 comprises an outer housing 60, which is preferably made of thermal plastic or another suitably rugged yet relatively lightweight material. A carrying handle, designated generally as 62 in FIG. 2, is integrally formed into the front of housing 60. With handle 62, programmer 20 can be carried like a briefcase.

An articulating display screen 64 is disposed on the upper surface of housing 60. Display screen 64 folds down into a closed position (not shown) when programmer 20 is not in use, thereby reducing the size of programmer 20 and protecting the display surface of display 64 during transportation and storage thereof.

A floppy disk drive is disposed within housing 60 and is accessible via a disk insertion slot (not shown). A hard disk drive is also disposed within housing 60, and a hard disk drive activity indicator, (e.g., an LED, not shown) is provided to give a visible indication of hard disk activation.

As would be appreciated by those of ordinary skill in the art, it is often desirable to provide a means for determining the status of the patient's conduction system. Programmer 20 is equipped with external connectors 24 that may be used to connect to pads placed on the patient's body to detect ECG tracings from the implanted ECG leads.

In accordance with the present invention, programmer 20 is equipped with an internal printer (not shown) so that a hard copy of a patient's ECG or of graphics displayed on the programmer's display screen 64 can be generated. Several types of printers, such as the AR-100 printer available from General Scanning Co., are known and commercially available.

In the perspective view of FIG. 2, programmer 20 is shown with articulating display screen 64 having been lifted up into one of a plurality of possible open positions such that the display area thereof is visible to a user situated in front of programmer 20. Articulating display screen is preferably of the LCD or electro-luminescent type, characterized by being relatively thin as compared, for example, a cathode ray tube (CRT) or the like.

As would be appreciated by those of ordinary skill in the art, display screen 64 is operatively coupled to the computer circuitry disposed within housing 60 and is adapted to provide a visual display of graphics and/or data under control of the internal computer.

Programmer 20 described herein with reference to FIG. 2 is described in more detail in U.S. Pat. No. 5,345,362 issued to Thomas J. Winkler, entitled *Portable Computer Apparatus With Articulating Display Panel*, which patent is hereby incorporated herein by reference in its entirety. The Medtronic Model 9790 programmer, inter alia, is the implantable device-programming unit with which the present invention may be used to determine the efficacy of the algorithms to be described below.

Figure 3:
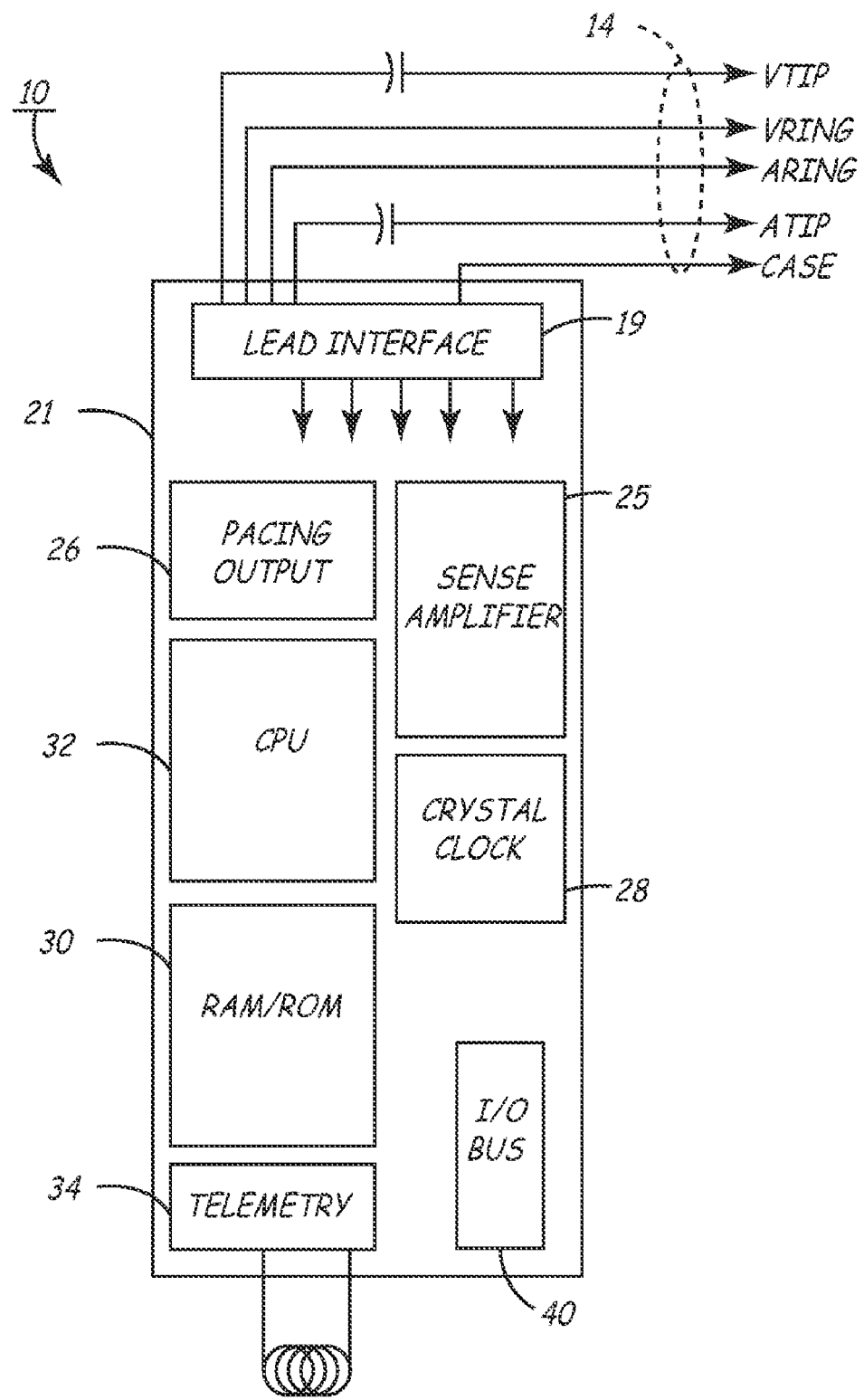
FIG. 3 is a block diagram of the implanted device from FIG. 1.

FIG. 3 is a block diagram of the electronic circuitry that typifies pulse generator 10 in accordance with the presently disclosed invention. As can be seen from FIG. 3, pacemaker 10 comprises a primary stimulation control circuit 21 for controlling the device's pacing and sensing functions. The circuitry associated with stimulation control circuit 21 may be of conventional design, in accordance, for example, with what is disclosed U.S. Pat. No. 5,052,388 issued to Sivula et al., *Method And Apparatus For Implementing Activity Sensing In A Pulse Generator*. To the extent that certain components of pulse generator 10 are conventional in their design and operation, such components will not be described herein in detail, as it is believed that the design and implementation of such components would be a matter of routine to those of ordinary skill in the art. For example, stimulation control circuit 21 in FIG. 3 includes sense amplifier circuitry 25, stimulating pulse output circuitry 26, a crystal clock 28, a random-access memory and read-only memory (RAM/

ROM) unit 30, and a central processing unit (CPU) 32, all of which are well-known in the art. Pacemaker 10 also includes internal communication circuit 34 so that it is capable of communicating with external programmer/control unit 20, as described in FIG. 2 in greater detail.

Further referring to FIG. 3, pulse generator 10 is coupled to one or more leads 14 which, when implanted, extend transvenously between the implant site of pulse generator 10 and the patient's heart 16, as previously noted with reference to FIG. 1. Physically, the connections between leads 14 and the various internal components of pulse generator 10 are facilitated by means of a conventional connector block assembly 11, shown in FIG. 1. Electrically, the coupling of the conductors of leads and internal electrical components of pulse generator 10 may be facilitated by means of a lead interface circuit 19 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components of pulse generator 10, as would be familiar to those of ordinary skill in the art. The specific connections between leads 14 and the various components of pulse generator 10 are not shown in FIG. 3, although it is known by those of ordinary skill in the art that, for example, leads 14 will necessarily be coupled, either directly or indirectly, to sense amplifier circuitry 25 and stimulating pulse output circuit 26, in accordance with common practice, such that cardiac electrical signals may be conveyed to sensing circuitry 25, and such that stimulating pulses may be delivered to cardiac tissue, via leads 14. Also not shown in FIG. 3 is the protection circuitry commonly included in implanted devices to protect, for example, the sensing circuitry of the device from high voltage stimulating pulses.

As previously noted, stimulation control circuit 21 includes central processing unit 32 which may be an off-the-shelf programmable microprocessor or micro controller, but in the present invention is a custom integrated circuit. Although specific connections between CPU 32 and other components of stimulation control circuit 21 are not shown in FIG. 3, it will be apparent to those of ordinary skill in the art that CPU 32 functions to control the timed operation of stimulating pulse output circuit 26 and sense amplifier circuit 25 under control of programming stored in RAM/ROM unit 30. It is believed that those of ordinary skill in the art will be familiar with such an operative arrangement.

With continued reference to FIG. 3, crystal oscillator circuit 28, in the presently preferred embodiment a 32,768-Hz crystal controlled oscillator provides main timing clock signals to stimulation control circuit 21. Again, the lines over which such clocking signals are provided to the various timed components of pulse generator 10 (e.g., microprocessor 32) are omitted from FIG. 3 for the sake of clarity.

It is to be understood that the various components of pulse generator 10 depicted in FIG. 3 are powered by means of a battery (not shown) that is contained within the hermetic enclosure of pacemaker 10, in accordance with common practice in the art. For the sake of clarity in the Figures, the battery and the connections between it and the other components of pulse generator 10 are not shown.

Stimulating pulse output circuit 26, which functions to generate cardiac stimuli under control of signals issued by CPU 32, may be, for example, of the type disclosed in U.S. Pat. No. 4,476,868 to Thompson, entitled *Body Stimulator Output Circuit*, which patent is hereby incorporated by reference herein in its entirety. Again, however, it is believed that those of ordinary skill in the art could select from among many various types of prior art pacing output circuits that would be suitable for the purposes of practicing the present invention.

Sense amplifier circuit 25, which is of conventional design, functions to receive electrical cardiac signals from leads 14 and to process such signals to derive event signals reflecting the occurrence of specific cardiac electrical events, including atrial contractions (P-waves) and ventricular contractions (R-waves). CPU provides these event-indicating signals to CPU 32 for use in controlling the synchronous stimulating operations of pulse generator 10 in accordance with common practice in the art. In addition, these event-indicating signals may be communicated, via uplink transmission, to external programming unit 20 for visual display to a physician or clinician.

Figure 4:
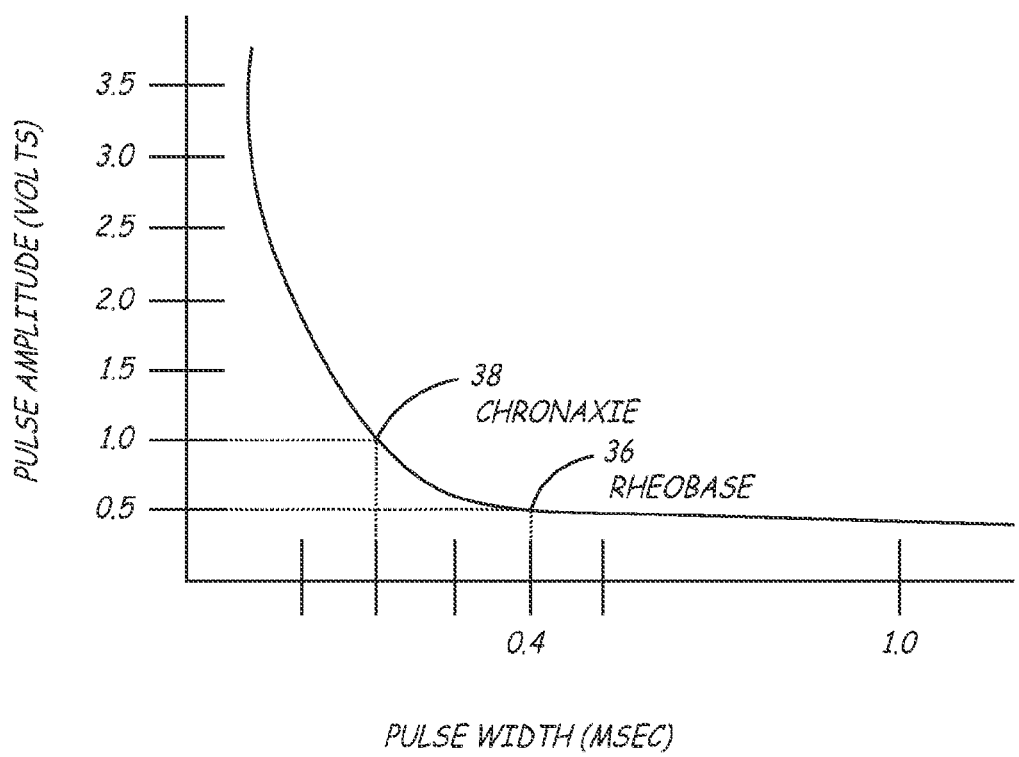
FIG. 4 is a typical strength-duration (S-D) curve for cardiac stimulation signals.

FIG. 4 shows a typical S-D curve for electrical stimulation of myocardial tissue plotted as pulse amplitude versus pulse width corresponding generally to FIG. 5 of the above-referenced '615 patent. The graph shows, inter alia, that the voltage required for stimulation increases with decreasing pulse width. Note, however, that beyond the Rheobase 36, further reductions in the amplitude may be insignificant so far as a voltage threshold is concerned. Thus, using a pulse width beyond 1.0 milliseconds, in some devices, or generally beyond 0.4 milliseconds in other devices, would not require a significantly greater voltage to capture the heart, (e.g. 0.5 volts in FIG. 4). Also included on the graph is Chronaxie 38, the point representing the lowest pulse width needed to provide stimulation at twice the voltage of Rheobase.

Those familiar with the art understand the manner in which thresholds are taken that involve a two-point test. Typically, a two-point test requires the determination of the rheobase point and then the chronaxie point. Because physiological changes in the patient may alter the thresholds from the initial measured value or values, good medical practice dictates that a safety margin be maintained. The calculation of an automatic safety margin after the determination of a rheobase and chronaxie that provide atrial or ventricular capture utilizes methods similar to those used in the Medtronic® Kappa® 700 pacing device. Each measured threshold may be multiplied by a predetermined safety margin, as is described in U.S. Pat. No. 5,447,525 issued to Powell, et al. In that patient the pacemaker chooses the voltage-pulse width pair having a lower associated current drain as the pacing output that is compliant with the desired safety margin.

In addition to a two-point test, the present invention may also use a single point determination of capture. That is, either a sequential search method to change the amplitude to determine rheobase alone, or a change of the pulse width to calculate chronaxie alone may be implemented. Thus, the one point test is a measurement of only either the rheobase or the chronaxie. Under this approach, either threshold value may be multiplied by a predetermined safety margin to obtain the desired output pulse.

During an ACR and AVC threshold test, a sequential search is used to calculate the point at which capture is lost or gained. To determine either rheobase or chronaxie, a sequential search can start at either the highest or lowest value of pulse amplitude or pulse width and continue through the range of middle values until it reaches the opposite pole. For example, a sequential search may start at the lowest amplitude and proceed to the highest amplitude setting, or from highest to lowest to arrive at rheobase 36. In the alternate, to determine chronaxie 38, the sequential search can start at the highest PW and go to the lowest, or search from lowest to highest. To ensure an accurate threshold measurement, each method requires that atrial capture and loss of capture be present Assessing capture and loss of capture at the same pacing value in two of three successive test paces increases the accuracy of capture detection method, by eliminating single case errors that could potentially occur due to random (PVC, PAC) change in the patient's rhythm.

Figure 5A:
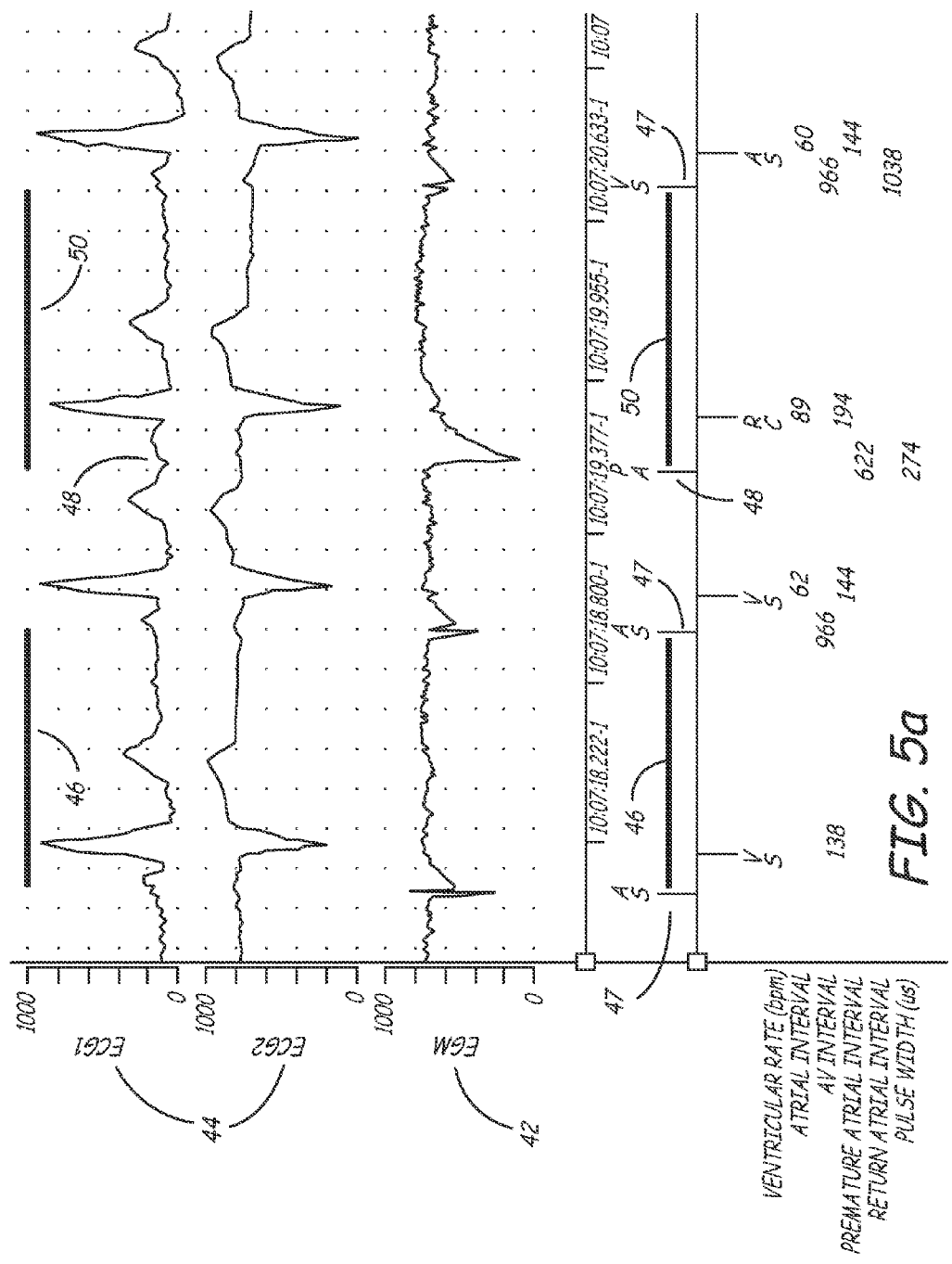
FIG. 5a is a display of ECG and EGM tracings showing capture by an Atrial Pacing Test (APt) pulse during ACR.

FIG. 5a is a display of ECG and EGM tracings showing capture by an APt (Atrial Pulse test pulse) pulse during ACR. EGM 42 displays atrial depolarizations that can be seen on the pacing electrode level. The difference in depolarization signals on EGM 42 is easily seen in waveforms appearing above atrial sense signals 47 and an early APt pulse 48. ECG tracings 44 are from different vectors, and typify those which are commonly found in a 12-lead ECG tracing. On ECG tracings 44, we have two intervals. Interval 46 is the reference atrial interval before APt pulse 48, whereas interval 50 is the "return" atrial interval that occurs after the premature APt pulse 48.

During ACR, a relatively stable sinus-driven rhythm is present. ACR is intended for use with those patients who have a "stable" sinus rhythm. That is, even before ACR is performed a series of stable cycles must be detected. More specifically, these AS-AS cycles are represented as interval 46 in FIGS. 5A-6. In practice, a number of these cycles must be observed before proceeding with ACR. For example, 3-10 consecutive stable cycles will indicate overall stability and allow for the APt pulse 48 to be initiated. The threshold level (degree of stability) and associated tolerance for determining stability may be selected to accommodate different factors. In general, there will be a trade-off between minimizing false events and maximizing patient applicability. That is, by requiring a high tolerance and determining instability if a given cycle is outside the narrow window, false events are minimized. However, there will then be a corresponding number of patients whose otherwise normal parameters will fall outside of these tolerances and who would have accurately tested but for the selection of the tolerances.

Thus, the programmer 20 can be used to adjust these tolerances based on clinical data. In this manner, the proper proportions can be maintained by maximizing patient applicability while minimizing false events by setting the appropriate tolerances. In other words, what constitutes a stable cycle can be modified over time. This same approach is applicable to AVC, as discussed below.

ACR is complementary to the AVC method in that patients do not usually have both SND and AV block. In ACR, if APt pulse 48 is subthreshold, the subsequent AS 47 occurs at the previous, stable interval (see FIG. 5b). If APt pulse 48 is above the threshold, then it captures and resets the sinus and there is no AS at the normal interval, as shown in this figure.

A-A interval 46 represents the last in a series of stable atrial rhythm intervals. In the example shown, A-A intervals 46 at 955 ms and 50 at 1038 ms have approximately the same duration. After capture by an APt pulse 48, the return A-A interval 50 is usually a little longer than the reference A-A interval 46. This is due to the time it takes for the atrial depolarization wave (typically initiated by the atrial electrode lodged in the atrial appendage) to travel to and reset the SA node, plus the time for the next sinus-initiated wave to travel from the SA node to the atrial electrode. During the previous several seconds, the sequential sweep operation had increased the output of APt pulse until it captures the atrium at 48. At this time, the stable atrial rhythm is also interrupted only to resume again at end of interval 50. This interruption by an early APt pulse, followed by resumption of the previous stable rhythm at or close to the previous rate, determines the magnitude of the atrial output pulse required to capture the atrium.

As mentioned, before initiating an APt 48 a series of stable cycles are required. In addition, there should also be a series of stable cycles (e.g., 3-4) or support cycles between each sequential APt 48 given during ACR. The purpose is to allow the heart to re-stabilize between test pulses. We previously described the variability in this sequence; thus, this variability in combination with the natural variations in the normal cardiac cycle will lead to some variation in measured AS-AS intervals. As such, some variation between the duration of the support cycles is to be expected and poses no concern. If however, there are wider swings in duration than might be expected then a problem could occur. That is, if the last monitored support cycle is particularly short (yet the measured sequence is still within the acceptable parameters) and then the APt 48 pulse is generated and captures, the result is two adjacent irregular intervals, which could trigger patient symptoms. To avoid such a situation, the support cycles are monitored for overall stability, but are also compared to one another. If the last monitored support cycle is not within a predetermined variation of either the previous support cycle (or alternatively an average of the most recent support cycles) then the support cycle monitoring routine is repeated. That is, the variant support cycle become the first in a new sequence of monitored support cycles and the APt 48 is only delivered when a full set is completed successfully. Alternatively, the first support cycle after the variant support cycle begins the next sequence. In addition, when such a support cycle is deemed an inappropriate variant, the abort counter is increased by an appropriately weighted amount.

To determine if the last support cycle before the APt 48 is appropriate, its duration may be compared to the duration of the penultimate support cycle. If the duration of the last support cycle is sufficiently close to that of the penultimate support cycle, the APt is permitted. The last support cycle and the penultimate support cycle should be within 50-150 ms of one another. In one embodiment, the two support cycles must be within about 100 ms of one another in duration. In this manner, an APt 48 is not delivered at a time when it would result in two sequential irregular atrial intervals.

Thus, during this process 3-4 such support cycles may be monitored and compared. If the last support cycle is irregular, the process is restarted and the abort counter is incremented appropriately. In addition, it may be possible to detect an earlier irregular interval (within the measured sequence) as well. Thus, in one embodiment if an earlier irregular interval is noted (which may only be determinable as the later intervals are measured), the process can be restarted from the first regular interval noted. In other words, the sequence of measured intervals does not need to be completed before action is taken to restart the support cycle monitoring routine. In this manner, the support cycles may be more stable prior to actually delivering the APt 48.

Figure 5B:
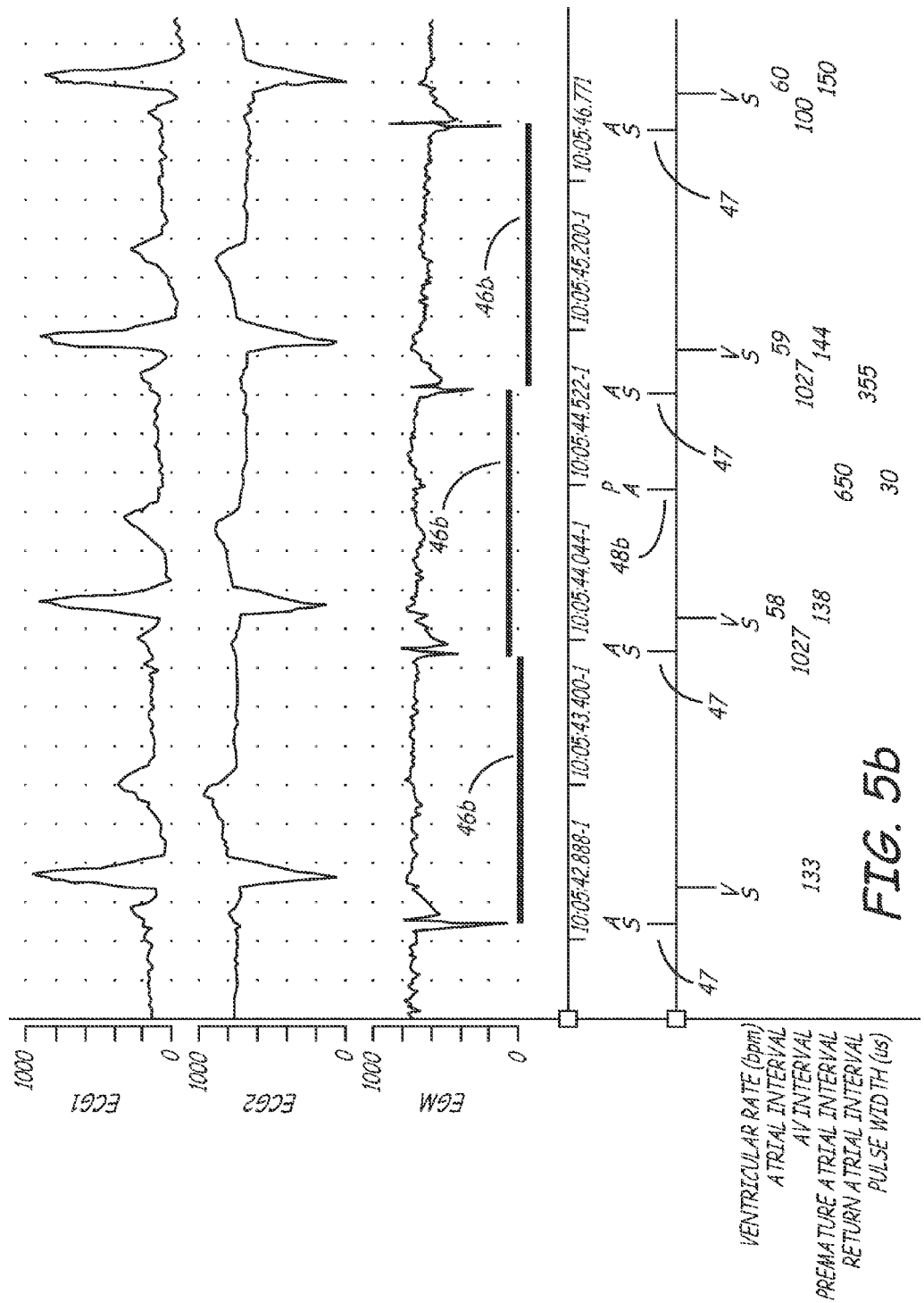
FIG. 5b is a display of ECG and EGM tracing showing LOC by an APt pulse during ACR.

FIG. 5b is a display of ECG and EGM tracing showing Loss of Capture (LOC) by an APt pulse 48b during ACR. As in FIG. 5a, Intervals 46b represent a stable atrial rhythm. In the example shown, A-A intervals 46b have approximately the same duration (1027, 1027, and 1000 ms respectively). APt pulse 48b, however, fails to capture the atrium.

Although the sequential sweep increased the output of the test atrial pace, APt pulse 48b does not capture the atrium. Therefore, the stable atrial rhythm continues without interruption. The algorithm recognizes the lack of interruption in the stable rhythm and "instructs" the sequential sweep to increase the atrial output for the subsequent test sequence.

Figure 6:
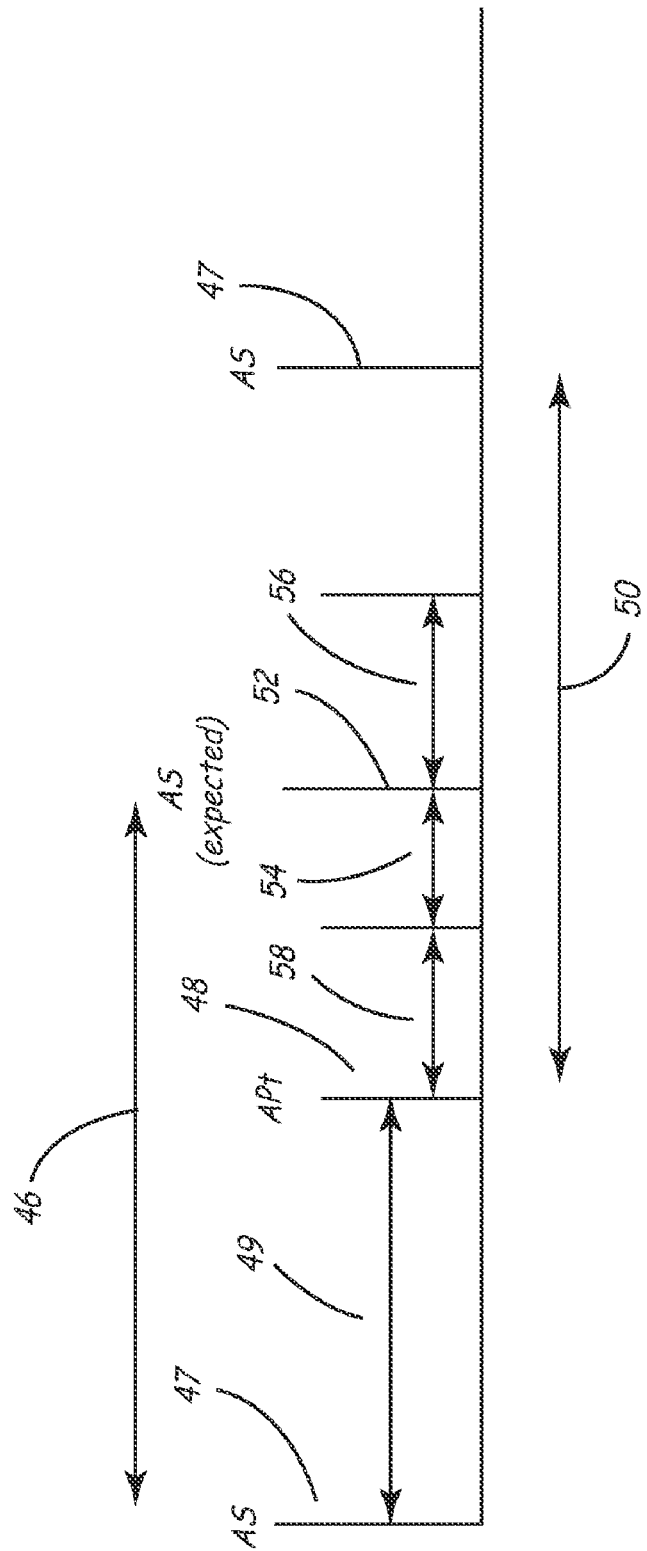
FIG. 6 is a timing diagram that typifies the various intervals that correspond to FIG. 5.

FIG. 6 is a timing diagram illustrating the various intervals that correspond to FIGS. 5a and 5b. Interval 46 corresponds to an atrial reference interval, that is, one that begins with and ends with an atrial sense. APt pulse 48 occurs at interval 49 and may or may not capture the atrium, depending on its magnitude. Two of three such consecutive test cycles with APt pulses of the same magnitude must capture the atrium to satisfy the algorithm that a stable atrial capture has occurred.

AS (expected) 52 will occur at the prevailing sinus rate (for example, 60 bpm) if the atrium is not captured and reset by APt pulse 48. The interval from APt pulse 48 to the AS (expected) will be short, that is the time of (interval 58+interval 54). If on the other hand, the interval from the APt pulse 48 to next atrial sense is longer, that is, the time of from APt 48 to the AS 47 at the end of FIG. 7 (Interval 50), capture of the atrium by APt pulse 48 has clearly occurred.

In addition to the above, the algorithm must also take into account the normal physiologic variation in a patient's sinus rhythm. To accommodate this variation, interval 54 starts 10 bpm faster than the previous AS-AS interval, which in this example could be 60 minus 70 bpm (or 1000 minus 857 ms). Interval 54 may also be described as a "negative" sensing interval, and is generally not less than some physiologic tolerance (~50 ms.) Interval 56, on the other hand, may be described as a "positive" sensing interval and is generally of the same duration as the "negative" interval. Intervals 54 and 56, taken together, can be termed the "LOC detection window." Atrial events sensed in the LOC detection window mean that the atrial test pace did not capture the atrium. As a result, if an AS (expected) event 52 occurs in the LOC detection window (and 2-of-3 rules were met), the atrial pulse output will be increased on the next sequential sweep. Interval 58 is a blanking interval following an atrial pace during which the atrial sense amplifier is unable to sense any electrical activity in the atrium. Interval 50, started by APt pulse 48, corresponds roughly in duration to interval 46, signifying atrial capture that reset the atrium (with perhaps some lengthening due to intra-atrial conduction delay times corresponding to time required for the pacing pulse emitted from the atrial lead to travel to the sinus node and for the subsequent atrial sense originating from the sinus node to the atrial lead). Thereafter, the cycle will start again. The stability of the atrial rhythm must again be established before another APt pulse 48 is delivered or ACR is terminated when at least two of three test paces have captured. Once at least two of three test paces have captured the atrium and a threshold has been determined, a safety margin can be calculated and put into effect.

In addition, a methodology is provided to determine a result if both an atrial sense (AS) and a ventricular sense (VS) occur within the same sensing window illustrated in FIG. 6. Furthermore, this method also will determine the presence of Far Field R-Waves. Such considerations are used to evaluate capture, loss of capture, or an ignore condition where no decision about capture is made. In addition, these considerations are used to affect an abort counter (discussed below) that will terminate the ACR function. Briefly, the abort counter records certain events that lead to the termination of the testing function for a specified period of time. For example, the detection of certain cardiac events or instability may be considered an abort criteria. These criteria will be weighted differently and the counter will terminate the testing when the accumulated count satisfies a predetermined value.

This methodology is based on the specific events that are sensed during the specific time windows. More accurately, this is reflected by a particular combination of sensed events. If an Atrial Refractory sense (AR) or Ventricular Refractory sense (VR) is detected during interval 58, the abort count is increased by the appropriate weighted value; however, this will not necessarily preclude a determination as to whether there was capture for the APt 48 in question. That is, if there is no AS in the LOC detection window (intervals 54 to 56), then the APt 48 has captured. The same is true if there was no VS; however, an AP would then be generated at the end of interval 56. If an AS and an AR both occur during the LOC detection window, then the abort counter is increased and a determination regarding capture is not made. The same result occurs if an Ventricular Sense (VS), VR and any one of a AR, AS, or Atrial Pace (AP) occur.

If there is an AS and a VS in the LOC detection window that are less than about 80 ms apart, the APt 48 is considered either a Far Field R Wave or a PVC, which are indeterminable from one another in this context. In either case, the abort counter is incremented and no determination of capture or loss of capture is made. If there is an AS and a VS (in either order) in the LOC detection window that are more than about 80 ms apart, the VS is assumed to have been conducted from the AS, thus loss of capture is determined. Finally, if an AS is detected in the LOC detection window and no VS occurs in the same interval, loss of capture is determined.

The following chart summarizes certain of the above parameters:

|  | AS in LOC detection window | | |
| --- | --- | --- | --- |
| VS in LOC detection window | Yes | If close together: Abort. If apart: LOC | Yes |
| VS in LOC detection window | Yes | VS in LOC detection window | Yes |

Referring again to FIG. 6, when APt 48 is generated, capture is determined by the absence of an AS during an expected time interval. That is, if no AS is noted during the LOC detection window, it is presumed that the APt 48 captured the atrium. If an AS is present but not detected, APt 48 will be deemed to have captured when in fact it did not. This is referred to as a false positive and is an unfavorable result. That is, the threshold may be set based on the false positive if the error is confirmed through subsequent erroneous determinations. Consequently, the IMD 10 may then pace below a threshold that achieves capture. Thus, it is desirable to avoid false positives.

One reason that false positives may occur is if the sense amplifier detecting the AS is effectively overwhelmed by the APt 48. That is, the APt 48 is on the order of a few volts (e.g., 3 volts) and the AS in on the order of a few millivolts. The same lead that is used to deliver the relatively large pulse is then used to sense the relatively small atrial event. This problem is worsened when high polarization leads are used, as these leads have a capacitive effect that prolongs the effect.

After delivery of the pulse, the sense amplifier 25 that is used must recover before it can accurately and reliably sense the atrial event. The faster the recovery time, the higher the reliability. In addition, the sense amplifier 25 itself is able to determine when the sense amplifier 25 is stable. Thus, in one embodiment, the sense amplifier 25 signals when it is stable and this signal is compared to the appropriate sensing window (e.g., LOC detection window). Assuming the sense amplifier 25 is stable before the sensing window begins, the process proceeds as has been previously described; in general, absence of an AS indicates capture. If, on the other hand, the sensing window begins and then the sense amplifier 25 stabilizes, the absence of an AS is not considered a capture. Rather, the system recognizes the possibility that the AS could have occurred before the sense amplifier 25 stabilized and simply been undetected. The abort counter can be incremented and the APt 48 can be redelivered at the same levels, but APt 48 will not be assumed to have captured because of the risk of a false positive. If there is an AS detected within the shortened time window, this event is counted and the system safely considers the previous APt 48 to have failed to capture. Therefore, simply having the stabilization period extend into the sensing window will not necessarily cause every event to fail.

In another embodiment, sense amplifier 25 is chosen so that it reliably stabilizes within an acceptable time frame. For example, reliable stabilization within about 120 ms precludes or at least minimizes the risk from potential false positives because the sense amplifier 25 will generally be stable before the LOC detection window begins. Even if sense amplifier 25 occasionally exceeds this stabilization period, it should pose little problem so long as the problem is not repetitive. As previously mentioned, a single indication of capture would not cause the threshold levels to be set. Rather, capture must occur at those levels several times sequentially before they are set. Thus, a single anomalous false positive can be washed out.

Figure 7:
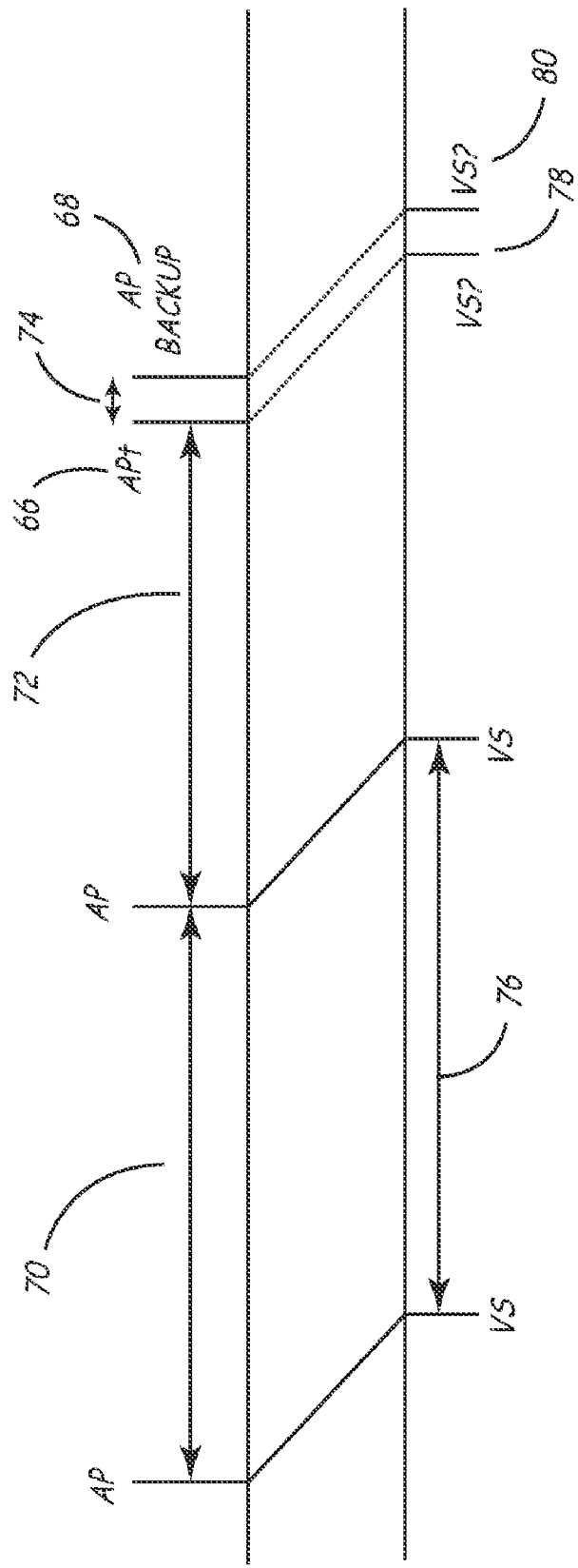
FIG. 7 is a general timing diagram that describes the AVC operation.

FIG. 7 is a general timing diagram that describes the AVC operation. In AVC, normally there is a stable atrial pace-ventricular sense (AP-VS) rhythm. A subthreshold atrial test pace will not capture the atrium and, as a result, the AP-VS rhythm is interrupted. If the test pace is above the atrial threshold, it will capture the atrium, resulting in earlier AV conduction and VS that is at 78 rather than at 80. Early conduction is the marker for capture in AVC. AVC is intended for those patients who have good AV conduction. Typically, these patients receive pacemakers for Sinus Node Disease (SND), or Sick Sinus Syndrome (SSS), among others.

Further referring to FIG. 7, interval 70 is the programmed AP-AP interval that, along with interval 76, demonstrates a stable AP-VS rhythm seen at times other than the AVC operation. Interval 72 begins with an AP at the programmed/calculated output setting but terminates early in APt pulse 66. In AVC, the sequential sweep can start with the greatest magnitude (ones that maintain capture) and decrement to those with the lower magnitude (ones that lose capture), atrial threshold search methods that start with low atrial outputs (that lose capture) and increment outputs until capture is restored are possible, but measurements below and above threshold are required to determine the threshold. AVC also times APt pulses 66 to be slightly premature and highly likely to maintain capture and then slowly reduces the magnitude of these test pulses so as to eventually lose capture. Interval 74 marks the measure of prematurity and terminates with atrial backup pacing pulse 68. The prematurity interval 74 will typically range between 50 to 100 ms. Backup pulse 68 does, in fact, occur at the overdrive AP-AP interval. If VS 78 occurs, the software/algorithm determines that APt pulse 66 has captured the atrium and further energy reduction of APt pulse 66 is required to lose atrial capture. Such further reduction in pulse magnitude occurs until a VS event occurs at 80, that is, the AP-VS time previously observed during stable rhythm. When this occurs, the algorithm determines that APt pulse 66 has lost capture. If loss of capture takes place in at least two of three consecutive complexes, the algorithm goes back to the last capturing output setting and uses this setting to calculate the safety margin.

Figure 8:
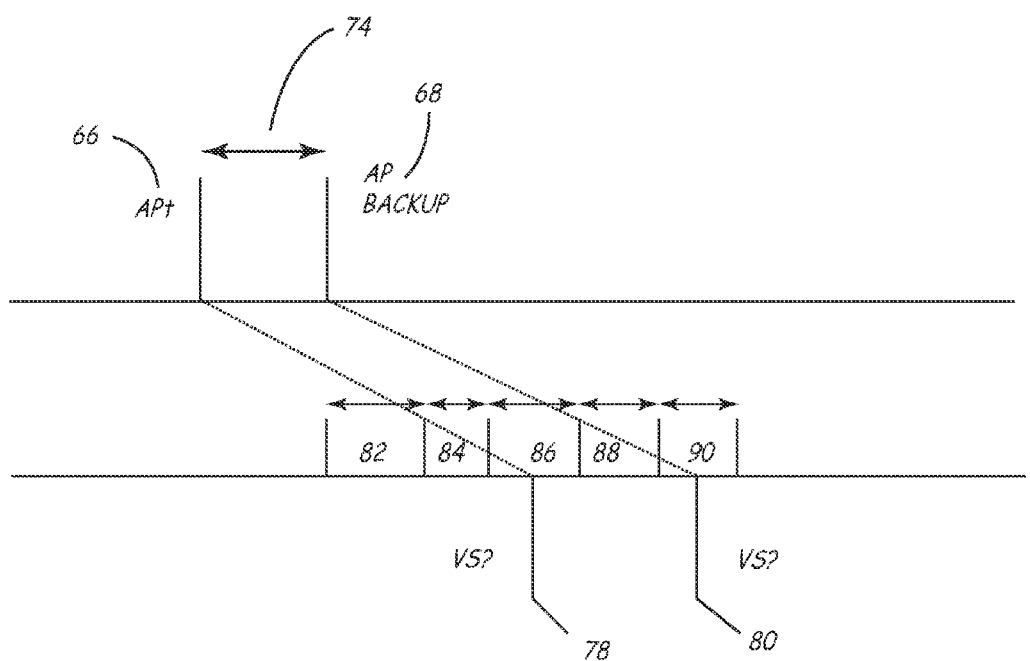
FIG. 8 is a detailed diagram of the AVC operation when an APt pulse captures the atrium.

FIG. 8 is a detailed diagram of the AVC operation when APt pulse 66 captures the atrium. APt pulse 66 is emitted and starts prematurity interval 74 leading to the emission of the scheduled atrial pacing pulse, here termed AP Backup 68. One of the purposes of AP backup 68 is to ensure capture when APt pulse 66 loses capture. There is no requirement that the patient be at rest for either operation to be successful. As in the case of ACR, the AVC operation may periodically emit a control pace (at output above the threshold) in the place of APt pulse 66 does not illicit a phenomenon AV conduction extension seen during increased atrial pacing and create a false negative ventricular sense at VS 80. If a VS 78 occurs on a control pace, AV conduction extension is not occurring, while a VS 80 occurrence on a control pace indicates AV conduction extension due to the slight prematurity of the control pace. The control pace is meant to eliminate a false negative, that is, one leading to the conclusion that APt pulse 66 actually lost atrial capture due to lack of conduction to the ventricle.

Interval 82 is the period during which the ventricular sense amplifier is blanked after Atrial backup pace 68. This is a function of the ventricular circuitry. Any ventricular event occurring during interval 84 is most likely due to cross talk. Any ventricular event occurring during interval 84 is ignored.

Interval 86 is the ventricular sensing window during which the algorithm looks for a sensed ventricular event. The algorithm assumes that any such sensed event during interval 86 is due to APt pulse 66. Further, any such ventricular sensed event would mean that the atrium had been captured and that the depolarization wave continues, from there, to the AV node and on to the ventricles. The duration of interval 86 is based on previous AP-VS intervals prior to the AVC operation. Interval 86 should be short enough to be specific in order to allow sensing of only those conducted events initiated by APt pulse 66. Further, interval 86 should be long enough to accommodate the normal variations in conduction time that occur. Interval 88 represents a variation in conduction from either APt pulse 66 or AP backup pulse 68. Interval 88 is wide enough so that any VS event occurring therein must be discounted. A VS within interval 88 will be ignored for purposes of capture and will constitute an abort criteria for potentially aborting the threshold search if a number of VS intervals are detected in interval 88. Because the AVC operation requires at least two of three ALOC events, an individual VS event within interval 88 would be ignored during AVC operation, whereas continued ventricular sensing in interval 88 would abort the AVC operation.

A VS event occurring in interval 90 means that the atrium was captured by AP backup pulse 68 and that APt pulse 66 failed to capture the atrium. Thus, interval 90 is referred to as the LOC window. In practice, the LOC window 90 will be set between approximately 5-100 ms in duration. Such ALOC either counts toward fulfillment of the two of three criteria, or fulfills that criterion. In the latter case, the algorithm uses the previous pulse magnitude that captured the atrium as a basis for calculating the appropriate safety margin.

When evaluating the timing for the prematurity window 74, the ventricular sensing window 86, and the LOC window 90, the granularity of the time base of the hardware must be considered. That is, any given window will simply be a multiple of the clock pulses utilized for timing, which is device dependant. As a further consideration, there should be a correspondence between the prematurity window 74 and the LOC window 90. In one embodiment, the duration of the LOC window 90 is less than or equal to the duration of the prematurity window 74. In this manner, a VS can accurately be determined to have originated from the APt 66 or the backup pace 68 that was initiated after the duration of the prematurity window 74.

Generally, after delivery of the APt 66 and the delivery of the AP backup 68 there should be a VS in either the ventricular sensing window 86 or the LOC window 90, dependent upon whether the first or second pulse captures. In some cases, no VS will be detected in either window (nor in the intermediate or precursor windows 82, 84 and 88). There are several ways to handle the lack of a VS.

In one embodiment, the lack of a VS is assumed to be a loss of capture and the processing proceeds with that assumption. Logically, it is assumed that the VS would occur at a later time had the LOC window 90 been extended. In an alternative embodiment, a failure to detect a VS causes the current event cycle to be ignored and the abort counter is incremented appropriately. This serves to improve threshold accuracy by utilizing and relying on stable and predictable rhythms and timing intervals and precludes using unexpected or anomalous events.

Figure 9A:
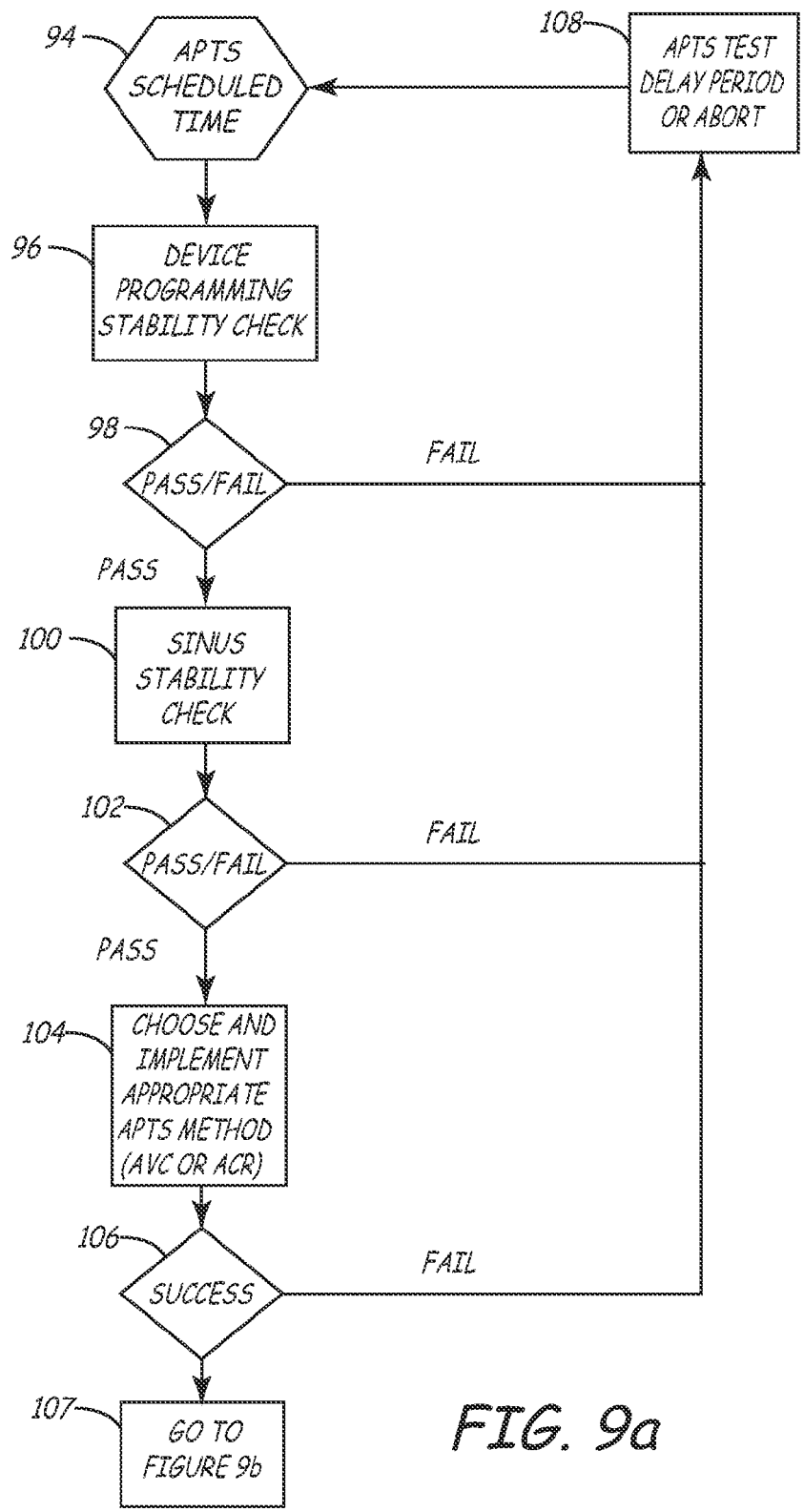
FIG. 9a is a flow diagram illustrating the first portion of the process for implementing either the AVC or ACR threshold test at the scheduled time.

FIG. 9*a* is a logic flow chart for implementing the selection process to use either the AVC or ACR threshold test at a scheduled time. Atrial Pacing Threshold Search (APTS) 94 is scheduled at a programmed period of time, such as "daily search," "daily fixed," or a period of time less than or greater than a 24-hour daily schedule. Upon scheduled APTS at step 94, the software program advances to check device stability at step 96. The device is qualified as a pass or fail at decision step 98. When the device is confirmed a pass, the software logic advances to sinus stability check at step 100. Under decision step 102, sinus stability is qualified as a pass or fail If the check is a pass, the software logic proceeds to step 104 where the appropriate APTS method, AVC or ACR, is implemented. If the APTS is successfully implemented in accordance with decision step 106, the program proceeds to step 107. If at any of decision steps 98,102 and 106 the finding is a "fail," the program to step 108 where the process is repeated or the program aborted.

It is during the stability check 96 that is determined which APTS method (AVC or ACR) will be attempted first. That is, if atrial pacing and ventricular sensing is occurring then the AVC method is selected at step 104. Alternatively, if atrial sensing is found, then the ACR method is selected at step 104. Each APTS stands on its own merits. No record of previous tests is retained, since the patient's rhythm may have changed since the previous APTS. APTS requires a dual chamber, dual pacing and tracking mode (DDD or DDDR) to ensure effective and safe use of the algorithm. Programming check 96 includes the following:

A permanently programmed atrial amplitude less than or equal to 5.0 V,

A permanently programmed atrial pulse width less than or equal to 1.0 ms,

An atrial tracking device in the dual chamber (DDD/R) mode,

A device not currently in mode switch operation, or its detection or recovery phase, A device not currently in rate drop response operation, A device not currently in sleep decay or awake stages, and A device with a sensor indicated rate less than or equal to the activity of daily living rate, as well as a sinus rate less than or equal to 100 bpm.

Further, sinus stability check 100 takes place over 8 cardiac cycles following device programming check 96 and may preferably include the following:

No more than a single occurrence of a PVC,

No more than one AP/AS/AR—AS interval in Device Programming check 96 was shorter than 600 ms, The shortest AP/AS/AR—AS interval must fall within the programmable Sinus Variability Window (default=200 ms) and be within that programmed millisecond interval of the longest AP/AS/AR—AS interval (rate stability), No occurrence of a PVC or PAC run, No more than one ventricular safety pace (VSP), and No occurrence of a non-competitive atrial pace.

If this check is also satisfied, then the "selector" portion of the software program will first attempt to use the AVC method. If no results are achieved with the AVC method, the algorithm selects the ACR method.

If either part of the stability check fails for any reason and the algorithm detects that the delay period is active, then the stability checks are rescheduled to recur at the end of the delay period. If the delay period is not active, or all delay periods have been attempted, the APTS test is aborted until the next scheduled PTS period.

Other methods for choosing between ACR and AVC may be employed at step 104. Depending upon the success of previous attempts or based on other programmed criteria, an internal flag can be set to bias either towards ACR or AVC, assuming conditions are otherwise even for a selection between the two. For example, after successfully achieving one protocol, a bias can be flagged to select the same in the future. Also, as each of the AVC or ACR protocols may only be attempted a predetermined number of times per day (e.g., 3), the flag can be used to bias towards an untried protocol. For example, if AVC has been attempted several times without success, the flag can bet set to favor ACR at the next attempt.

Figure 11:
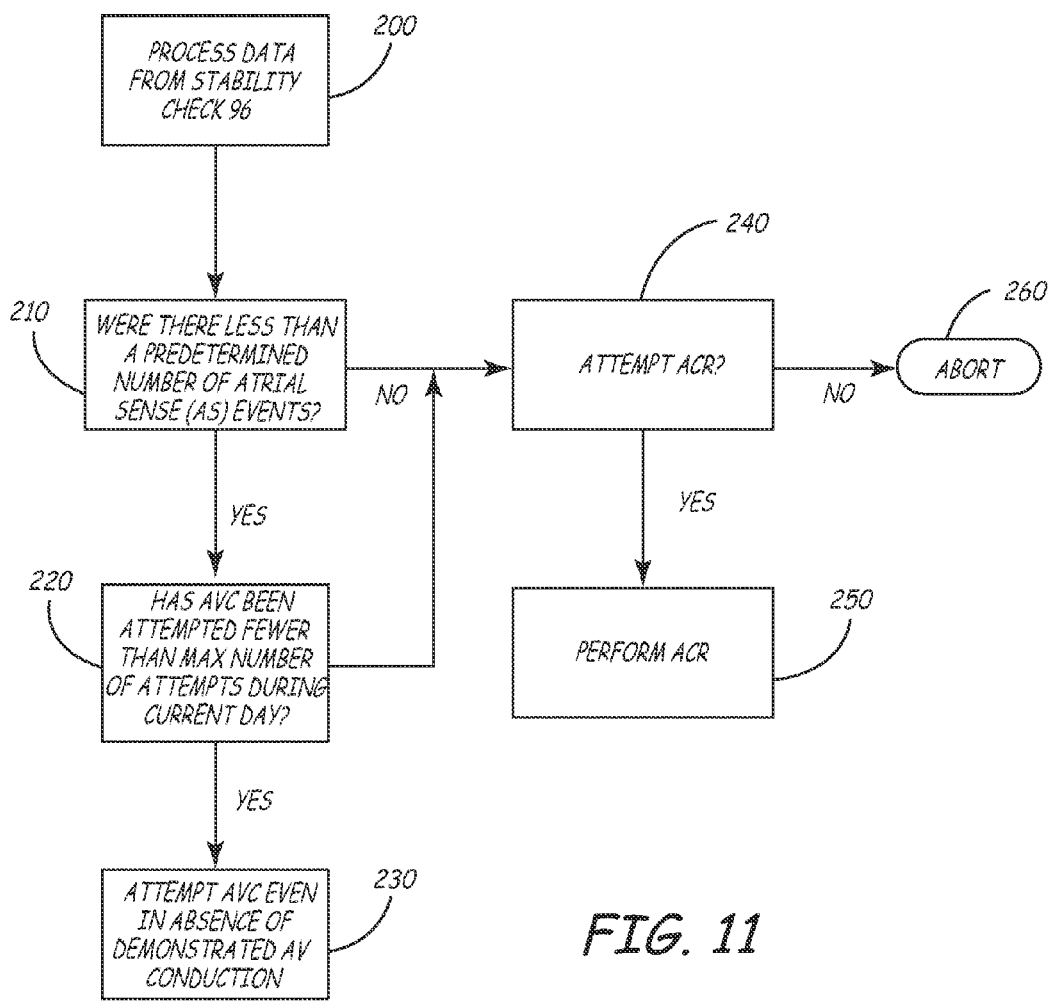
FIG. 11 is a flow diagram showing the process of selecting between ACR and AVC.

FIG. 11 illustrates a process for determining whether ACR or AVC should be utilized, with a bias towards AVC. As above, the stability check is performed at 96 and the data is processed at step 200. Assuming the stability check is successful, the process moves forward to attempt APTS. There could be several reasons why the stability check 96 would fail; for example, if sensed intervals vary by more than, for example, 125 ms, then the test will be delayed until a later time when stability is achieved.

In this instance, there is a bias to attempt AVC even in the absence of a demonstrated AV conduction. Thus, at step 210 it is determined if there were fewer than a predetermined number of atrial sense events (e.g., 7). If there are too few AS events, then ACR would likely be unsuccessful. If there were more than a predetermined number of AS events, a decision as to whether to conduct ACR is made at 240. Assuming there were fewer than the predetermined number of AS events, step 220 determines whether AVC has been attempted previously during the same day. If so, AVC will not be reattempted if the daily number of attempts (e.g., 3)

has already been made. If fewer than the maximum number of daily attempts for AVC have been made, then AVC is attempted at step 230. Otherwise, a decision as to whether or not to attempt ACR is made at step 240 and ACR is either conducted at step 250 or ACR is aborted at step 260.

Figure 9B:
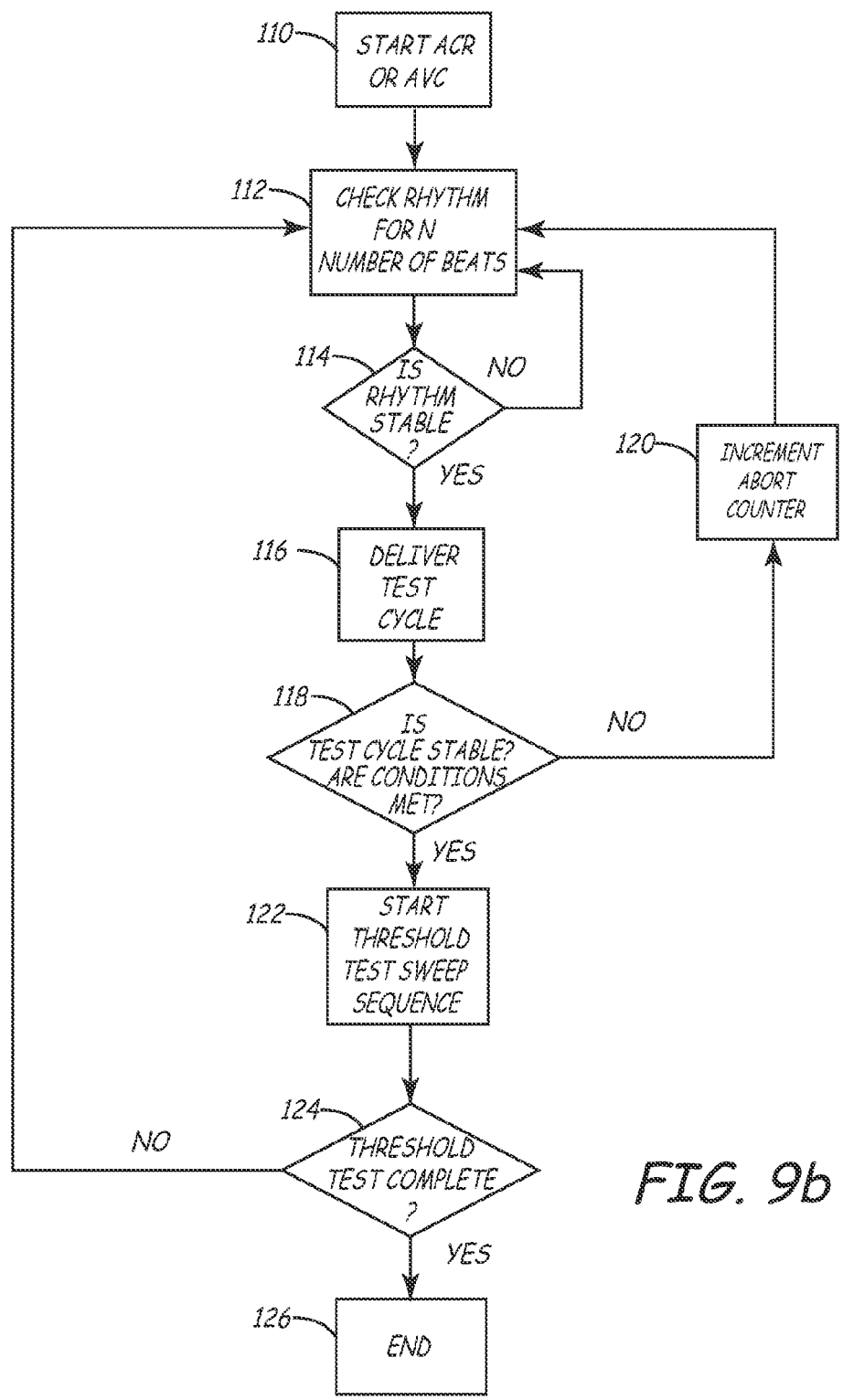
FIG. 9b is a flow diagram illustrating the second portion of the process for implementing the AVC or ACR threshold test at the scheduled time.

FIG. 9b illustrates a logic flow for implementing an AVC or ACR threshold test at a scheduled time. The operation is initiated at step 110. Subsequent step 112 checks rhythm for a set number of beats. The stability of the rhythm is confirmed at decision step 114. The software logic will not proceed forward until a stable rhythm has been established.

More specifically, upon choosing the appropriate APTS method 104 (FIG. 9A), either ACR or AVC begins at logic step 110. The algorithm checks the rhythm for either a preset or programmed number of beats 112. One of the purposes of step 112 is to determine whether the rhythm, which was previously recognized as stable 102 (FIG. 9), has remained stable at decision step 114. If the rhythm is stable, threshold test cycle is delivered at logic step 116. If test cycle integrity is unstable at any condition, the logic proceeds to logic step 120 where the abort counter is incremented. If abort counter is full then APTS is rescheduled consistent with logic step 92 (FIG. 9a). If abort counter is not full, the logic reverts back to step 112. If, on the other hand, all conditions are met at decision step 118, the algorithm starts the threshold test sweep sequence at step 122 consistent with the disclosure of FIGS. 4 through 8. Upon successful completion of the check to see that at least two of three test paces have captured the atrium, the threshold test proceeds to decision step 124. If the threshold test is completed at decision 124, the APTS threshold test is terminated at 126. If, however, at least two of three criteria are not met at decision step 124, the algorithm returns to rhythm check 112 and prepares for the next threshold test cycle.

In general, atrial capture management (ACM) is performed on a periodic basis, e.g., once per day, in order to determine an appropriate threshold level, as previously indicated. In order to properly determine the threshold level a certain degree of stability must be observed prior to initiating any test pulse and when determining if capture occurs. Without a stable rhythm, the risk of false measurements is increased. In order to assure higher accuracy in measurement and prevent the APTS from cycling and possibly generating patient symptoms, the abort counter of step 120 is utilized. The abort counter keeps a running count of certain triggering events and if a predetermined level of such events is reached, the APTS is aborted.

During each of the stability cycles (i.e., absent of test pulses) and test cycles, stability and various cardiac conditions are monitored. Such conditions include, for example, PVC's, PAC's, Ventricular Refractory Senses, Atrial Refractory Senses, AS-AS interval variability, and AP-VS interval variability. If instability or a condition is detected, the abort counter is incremented by a weighted value. The value is weighted based on severity as determined by a predetermined value for each instability or a given condition.

In general, when the abort counter exceeds the predetermined value and APTS is aborted, the system is prevented from reinitiating APTS for some predetermined period of time, e.g., 30 minutes. In addition, there may also be a daily limit to the number of attempts allowed, e.g., three. Thus, if unexpected conditions are encountered or the requisite stability is absent, the APTS can abort without determining a threshold value and if such conditions persist, may not find a threshold over the course of the entire day.

Figure 10:
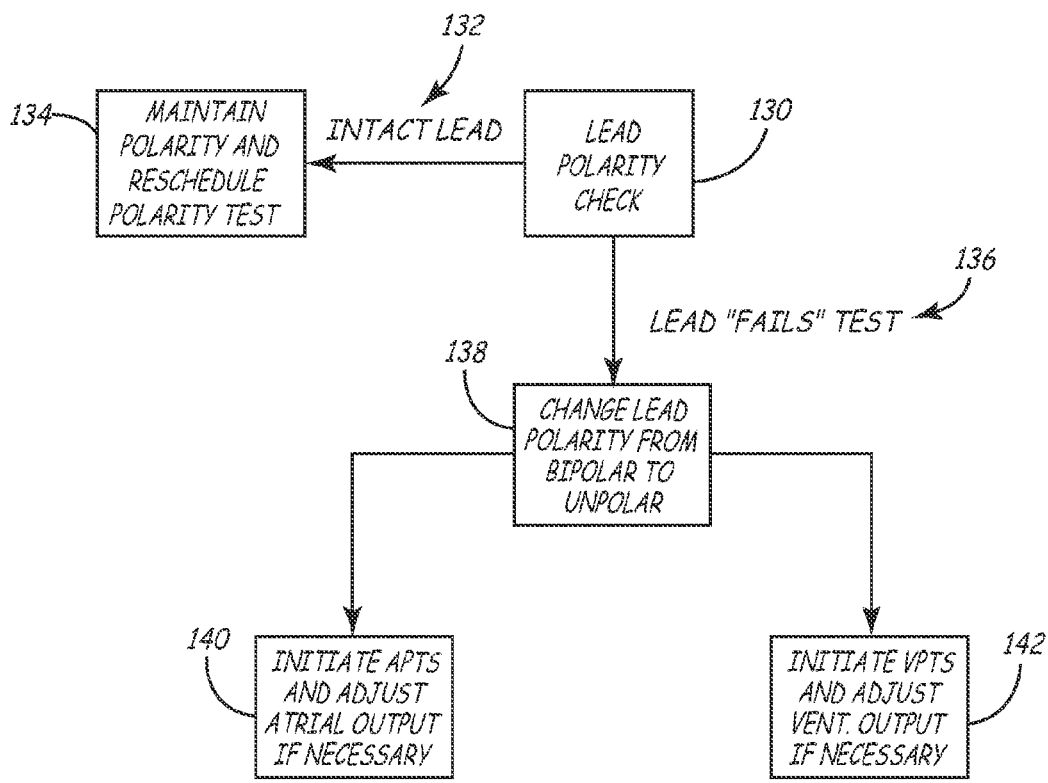
FIG. 10 is a flow diagram showing the process for a Pacing Threshold Search (PTS) on an atrial or ventricular lead following a switch from unipolar to bipolar upon detection of a "failed" lead.

FIG. 10 represents the process for PTS on an atrial or ventricular lead following a switch from bipolar to unipolar upon detection of a "failed" lead. Modern pacemakers include a circuit that periodically performs a lead check 130 to determine the integrity of the lead wire and associated structures. Currently, lead impedance is used to determine the integrity of bipolar leads. Other methods may include, for example, the detection of zero or excessive amounts of charge drained from the output capacitor and time domain reflectometry. If a lead polarity check indicates the lead to be intact under step 132, the lead polarity is maintained and the circuitry resets itself to conduct a polarity check at the next programmed or scheduled time in accordance with step 134. On the other hand, if the test is negative, the lead is deemed to have failed the test in accordance with step 136. For example, a lead that "fails" an impedance test will exhibit a very low (break in the insulation) or very high (break in the conducting wire) impedance. If it was in the bipolar configuration, failure of the lead at step 136 immediately changes lead polarity from bipolar to unipolar as in step 138. Upon change to unipolar configuration, pacing circuitry in accordance with the present invention immediately initiates PTS on either atrial channel at step 140 or ventricular channel at step 142, depending on which lead failed the polarity test. If the failed lead was unipolar, a message will appear indicating lead failure when the device is next interrogated.

One of the aspects of the present invention relates to atrial and ventricular pacing thresholds that may differ when pacing switches from bipolar to unipolar. If the output is below threshold values in the unipolar configuration, an immediate LOC may occur with the potential for syncope or death. If the output doesn't include a safety margin, LOC may occur when conditions vary, such as engaging in activities (exercise, eating, inter alia) that change the strength-duration curve as illustrated, for example, in FIG. 4. Thus, the above described APTS and automatic VPTS methods, will implement automatic means to determine a reliable safety margin for the pacing output.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than is specifically described, without departing from the scope of the present invention. As to every element, it may be replaced by any one of infinite equivalent alternatives, only some of which are disclosed in the specification.

The invention claimed is:

1. A medical device system comprising:
   means for monitoring atrial events and determining a number of detected atrial senses (AS); and
   means for selecting between atrial chamber reset (ACR) and atrial ventricular conduction (AVC), wherein the means for selecting will select AVC if the number of detected atrial senses (AS) is below a first predetermined value and a number of failed attempts of AVC for a current day is below a second predetermined values.

2. The system of claim 1, wherein the first predetermined value is seven.

3. The system of claim 1, wherein the second predetermined value is three.

* * * * *

UNITED STATES PATENT AND TRADEMARK OFFICE
CERTIFICATE OF CORRECTION

PATENT NO. : 7,280,868 B2  Page 1 of 1
APPLICATION NO. : 10/434689
DATED : October 9, 2007
INVENTOR(S) : John Rueter et al.

It is certified that error appears in the above-identified patent and that said Letters Patent is hereby corrected as shown below:

Col. 18, line 60, delete "predermined values" and insert in place there of --predetermined value--.

Signed and Sealed this

Sixth Day of January, 2009

JON W. DUDAS
*Director of the United States Patent and Trademark Office*